United States Patent [19]

Wittwer et al.

[11] Patent Number: 4,576,284

[45] Date of Patent: Mar. 18, 1986

[54] CLOSING OF FILLED CAPSULES

[75] Inventors: Fritz Wittwer, Lupsingen; Thomas Raible, Mohlin, both of Switzerland

[73] Assignee: Warner-Lambert Company, Morris Plains, N.J.

[21] Appl. No.: 557,306

[22] Filed: Dec. 2, 1983

[51] Int. Cl.⁴ .................... B65D 53/06; B65D 85/00
[52] U.S. Cl. .................................. 206/530; 206/528; 215/233
[58] Field of Search ............... 206/528, 529, 530, 820; 220/8; 215/233

[56] References Cited

U.S. PATENT DOCUMENTS

| | | | |
|---|---|---|---|
| 890,164 | 6/1908 | McKean | 215/233 |
| 941,538 | 11/1909 | Schies | 215/233 |
| 1,836,220 | 12/1931 | Bloom | 215/233 |
| 2,340,037 | 1/1944 | Zipper | 206/530 |
| 2,663,461 | 12/1953 | Brown | 206/820 |
| 3,653,500 | 4/1972 | Allisbaugh | 206/530 |
| 4,196,565 | 4/1980 | Bodenmann et al. | 206/530 |
| 4,250,997 | 2/1981 | Bodenmann et al. | 206/528 |

Primary Examiner—William T. Dixson, Jr.
Attorney, Agent, or Firm—Alan H. Spencer; S. Raines

[57] ABSTRACT

A hard shell capsule for the exact dosage of substances, especially for pharmaceutical use, having a body part and a cap part which is joinable with said body. The body part has a side wall, a closed end and an open end. The cap part is die-molded or extruded as a stopper directly into the open end of the body after the body has been filled, so as to seal the contents within the capsule.

5 Claims, 3 Drawing Figures

CLOSING OF FILLED CAPSULES

BACKGROUND OF THE INVENTION

The present invention relates to a hard shell capsule for the exact dosage of solid, creamy and liquid substances, especially for pharmaceutical use. The capsule has a cap part and a body part, said body part having a side wall, an open end and a closed end.

Due to the limitations of manufacture by the prior art dip-molding process, prior art capsules have telescopically joinable cap and body parts which require that the inner diameter of the cap side wall frictionally engage the outer diameter of the body side wall. When the cap and the body are joined, the open end of the cap forms a relatively sharp protruding edge on the outside surface. The prior art capsules also have the following principal disadvantages:

the capsules are neither tamper-proof nor separation-resistant if not provided with additional locking features. This is a major disadvantage if such a capsule, especially one containing food or drugs, can be opened or tampered with;

the capsules are not entirely leak-proof, especially when filled with creamy or liquid media; and the capsules are not sufficiently tight to prevent additional oxygen entrance into the capsule which may cause oxidation of the contents.

In U.S. Pat. No. 3,653,500 there is described a method for mating filled, sealed capsules: the body of the hard gelatin capsule is made by the conventional dip-molding process, then filled and finally a drop of molten gelatin is placed over the body's open end in contact with the filled material. In this prior patent the sealed capsules show edges on the top where the drop of molten gelatin has fused with the open end of the capsule body.

In the present invention, the following considerable improvements over the prior art are disclosed:

the capsule body is made by a dip-molding or by a die-molding process;

the cap part is die-molded or extruded onto the body part; and the capsule is tamper-proof and has a smooth outer surface.

It is an object of the present invention to provide a capsule with the aforementioned advantages.

It is another object of the present invention to provide a capsule which is liquid, moisture vapor and gas tight.

The advantages of the present invention will become apparent to those skilled in the art from a consideration of the detailed description which follows with reference to the accompanying drawings.

DETAILED DESCRIPTION

Figure 1:
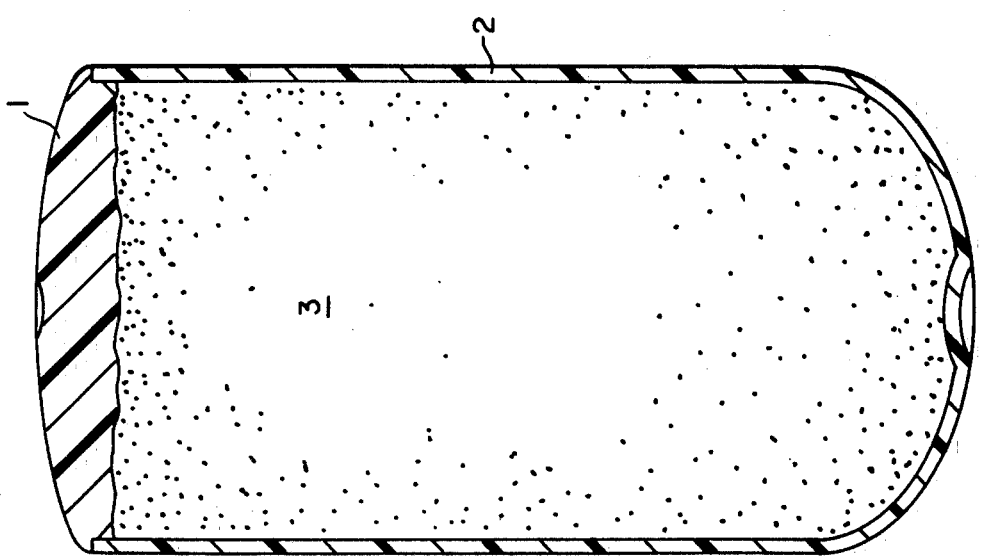
FIG. 1 is a longitudinal sectional view of an embodiment of the capsule of the present invention.

In FIG. 1 there is shown an embodiment of a capsule which might be filled with a pharmaceutical product to be swallowed by the patient. In this embodiment the cap-stopper 1 is formed by die-molding so as to provide a smooth outer surface when joined i.e. it has the same outer diameter as the capsule body 2 which is filled with the contents 3.

Figure 2:
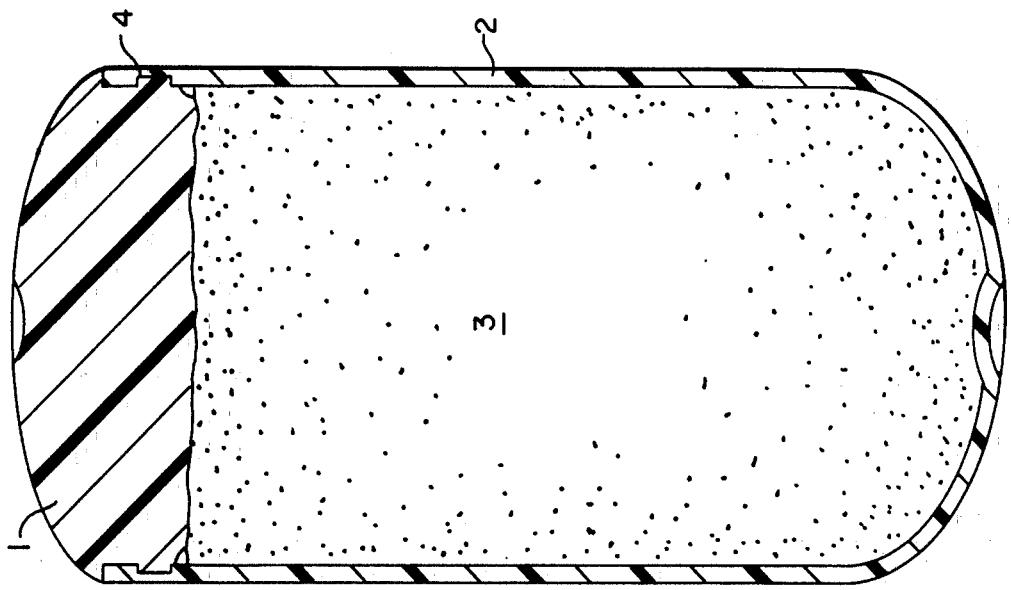
FIG. 2 is a longitudinal sectional view of another embodiment.

FIG. 2 shows another embodiment wherein a body 2 is provided with a groove 4 to assure the tightness of the stopper 1 when joined over the contents 3.

Figure 3:
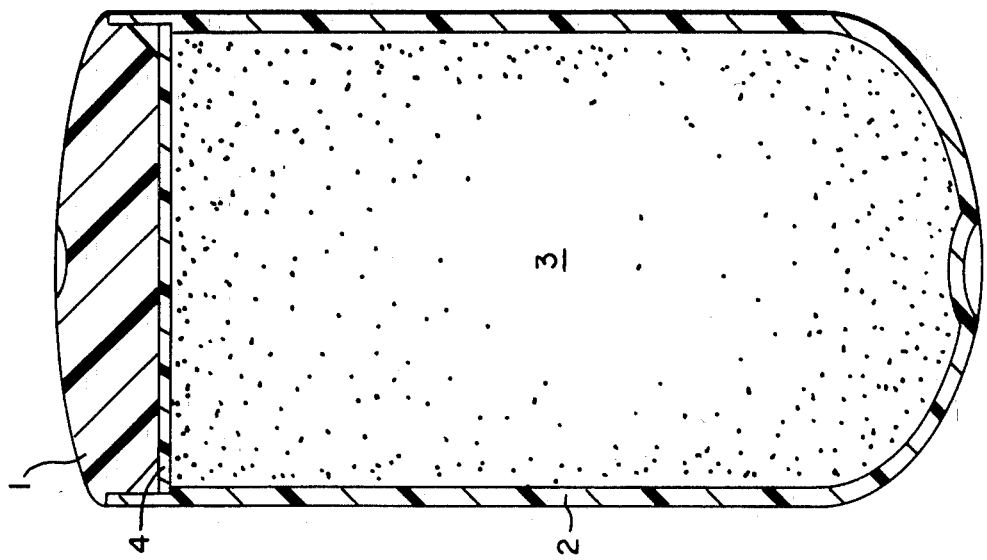
FIG. 3 is a longitudinal sectional view of a further embodiment.

In FIG. 3 there is shown a further embodiment wherein a flat, circular plate or disc 4 was inserted into the body 2, so as to completely cover the filling material 3. In this embodiment the stopper 1 is formed by die-molding so as to provide a smooth outer surface when joined, i.e. it has the same outer diameter as the capsule body 2 which is filled with the material contents 3. The cover plate 4 will permit injection molding of the closing stopper at a very high speed.

EXAMPLES

Example 1

A capsule body was die-molded on an injection molding machine. The material was bone gelatin, 150 Bloom, B grade, having a water content of 17% based on the weight of the composition. The material was plasticized at 130° C. and injected into a die at 20° C. The capsule body was then removed from the mold, filled with lactose and inserted into a second mold. The second mold was mounted in the injection molding machine wherein the stopper was injection molded onto the open end of the filled capsule body. The material of the stopper was the same as for the body. During injection molding of the stopper, a seal was formed between the stopper and the body so that the capsule was liquid, moisture vapor and gas-tight, as well as tamper-proof.

Example 2

A capsule body was die-molded on an injection molding machine. The material was bone gelatin, 150 Bloom, B grade, having a water content of 10% and a content of organic plasticizers: sorbitol of 6% and glycerol of 3%, all based on the weight of the gelatin. The material was plasticized at 130° C. and injected into a die at 18° C.

After removing the capsule body from the mold, it was filled with a creamy content, Labrafil ®, trademark owned and material supplied by Gattefosse, 39 Avenue Ed.-Vaillant, 92100 Boulogne, France, for C12 to C13 exthoxylated saturated glycerides. Then the procedure described in Example 1 above was followed.

The body parts of the present invention can be made either by dip-molding or by die-molding techniques. The cap-stopper parts of the present invention can be produced on injection molding machines wherein the capsule material is melted in a plasticizing unit and then injected into a mold directly into the open end of the body after the body has been filled and inserted into this mold. When the mold is opened, the capsules are ejected. As capsule materials, there may be used, for either of the capsule parts: gelatin, starch or other polymer materials, including mixtures thereof and foams of such materials whose properties are suitable to be die-molded or extruded.

In certain cases, especially with creamy or liquid capsule contents having the tendency to interact with the capsule wall, organic plasticizers are used: including glycerol, sorbitol, dioctylsodium sulfosuccinate, triethyl citrate, tributyl citrate, 1,2 propyleneglycol, mono-, di-, triacetates of glycerol at a concentration range of about 0.5 to about 40% based upon the weight of the polymer material.

Such plasticizers are also used for the manufacturing of soft gelatin capsules in order to resist to the above indicated interactions between the capsule wall and the capsule content.

Compression molding, blow molding and other die-molding or extruding techniques may also be used for the cap-stopper parts of the present invention.

In the present invention, the cap-stopper parts may be extruded with a hydrophilic polymer material having a water content in a range of about 5 to 30% by weight, and an extruded temperature in a range about 80° to 190° C.

All of the capsules produced in conformity with the present invention may be used for pharmaceutical purposes as well as for the exact quantitative dosage of dyestuffs, spices, fertilizing combinations for indoor plants, fertilizers with protective substances, seeds, cosmetics, agricultural products, etc.

It should be understood that this disclosure is for the purpose of illustration only and that the present invention includes all modifications and equivalents falling within the scope of the appended claims.

What is claimed is:

1. A hard shell capsule for the exact dosage of solid, creamy and liquid substances which comprises a body part, said body part having a closed end, a sidewall extending from said closed end, and an open end, said sidewall having an internal recess extending circumferentially around said sidewall, adjacent said open end and a cap molded in situ, said cap being in engagement with said recess, whereby said open end of said capsule is sealed subsequent to filling.

2. Capsule according to claim 1, characterized in that the cap part is formed by extrusion techniques at elevated temperatures and pressures.

3. Capsule according to claim 2, characterized in that the cap part is made from a hydrophilic polymer material having a water content in a range of about 5% to 30%, by weight, an extruded temperature in a range of about 80° to 190° C., and is extruded by a screw extruder as it is widely applied in polymer processing industries with a pressure range of about 50 to 1500 bars.

4. A capsule according to claim 1 further including a cover plate positioned in said recess under said cap.

5. A capsule according to claim 4 wherein the dosage fills less than the enclosed portion of said capsule.

* * * * *